United States Patent [19]

Sick et al.

[11] 4,180,702

[45] Dec. 25, 1979

[54] PHOTO ELECTRIC LIGHT DETECTION DEVICES

[75] Inventors: Erwin Sick, Icking; Klaus Hartmann, München; Heinz Henneberger, Stockdorf, all of Fed. Rep. of Germany

[73] Assignee: Erwin Sick Gesellschaft mit beschrankter Haftung Optik-Elektronik, Waldkirch, Fed. Rep. of Germany

[21] Appl. No.: 853,889

[22] Filed: Nov. 22, 1977

[30] Foreign Application Priority Data

Dec. 1, 1976 [DE] Fed. Rep. of Germany ....... 2654464

[51] Int. Cl.² ............................................. G02B 5/14
[52] U.S. Cl. .................................. 250/227; 250/209
[58] Field of Search .................. 250/227, 209, 208; 350/96 WG

[56] References Cited

U.S. PATENT DOCUMENTS

| 3,274,392 | 9/1966 | Harling | 250/227 |
| 3,501,632 | 3/1970 | Kaminskas | 250/227 |
| 3,777,149 | 12/1973 | Marcatili | 250/227 |

Primary Examiner—M. Tokar

[57] ABSTRACT

A photo electric light detection device comprising an array of photodiodes is disposed at an end face of a light conducting rod in order to produce an output signal proportional to light incident on the surface of the rod and transmitted to the end face by total internal reflection. The array of photodiodes is subdivided into high and low pass frequency sub-arrays and the output signals from the sub-arrays are summed and processed to compensate for stray light. The device is useful in connection with a line scanner for detecting anomalies in a moving band.

28 Claims, 5 Drawing Figures

PHOTO ELECTRIC LIGHT DETECTION DEVICES

The present invention relates to improvements in photo electric light detection devices and has particular reference to a photo electric detection device disposed at one end face of a light conducting rod for converting light received by the rod to electricity and an electronic processing unit for processing the electrical signals produced by the photo electric device.

Such detection devices are used for example with line scanning devices in which a sharply defined beam of light especially a laserbeam scans a band of material. The transmission, reflective or mismatch characteristics of the band at the position probed with the laser beam can be used to derive information about faults in the band.

In order to collect the light used for measurement, which is constantly probing the band at very different positions, at the convertor for light to electricity, light conducting rods are used whose surfaces are arranged in the area of the band which is being probed with the light beam.

It can be ensured, for example by the use of cylindrical lenses, that as much as possible of the remitted, reflected or transmitted light falls on to the surface of the light conducting rod. By total reflection inside of the light conducting rod a desired portion of the light entering the light conducting rod reaches the end faces of the light conducting rod where it is received by a converter for changing light to electricity. Converters from light to electricity can be arranged at both end faces of the light conducting rod. It is also possible to make one end face of the light conducting rod reflecting and simply to arrange a converter of light to electricity at the opposite end face of the light conducting rod.

Previously photoelectric multipliers, or photo multipliers were used as convertors of light to electricity in order to achieve a sufficiently strong electrical output signal. The disadvantage of the multiplier is however that it is relatively expensive, sensitive to vibrations and strong lights (such as sunlight), that it has disuniformities in the light responsive layer and that it also has a proportionally short useful life.

It is difficult to separate stray light from the light which is used for measuring and furthermore the response range of the photomultiplier is restricted to a value of approximately 40 db.

The present invention seeks to provide a photoelectric light detection device of the aforementioned kind by means of which the convertor for light to electricity is considerably less troublesome and expensive without loss of sensitivity, has a longer useful life and which is neither sensitive to straylight or to mechanical vibrations.

The apparatus should also have small physical dimensions and be of compact construction.

According to the present invention there is provided a photoelectric light detection device suitable for being disposed at one end face of a light conducting rod, and comprising an array of photodiodes, the diodes of the array being connected together to produce a single output signal and an electrical processor for processing the signal from the diode array.

Such diode arrays are not only very economical but have a practically unlimited useful life. They are relatively insensitive to mechanical vibrations and the influence of strong stray light. They deliver an output signal being a function of the light input in a range of 120 db so that considerable stray light levels can be accepted. The surrounding light can be simply separated by using one of the diodes of the array as a compensating diode by connecting it to a circuit including a special time element. A further advantage of the use of a diode array is that, in contrast to a photomultiplier, no high voltages are necessary.

Nevertheless, the efficiency obtained by using a diode array is not worse but rather better than with a photo electric multiplier. By the connecting together of the numerous diodes in an array an average value across the whole cross section of the light conducting rod can be obtained. The resolution can be exceptionally high and for a capacity compensated diode array lies in a range of 40 MHz.

In this manner the light detection device would compare favourably in every respect with the known light receiving device using a photomultiplier.

Preferably the diode array is disposed on a plate facing the end face of the light conducting rod. The plate can be manufactured in a separate process and then simply be incorporated into the light conducting rod. The form and size of the plate therefore preferably equate with the form and size of the cross-section of the light conducting rod.

Preferably the diode array is spaced from the end face of the light conducting rod. In this way a light scattering element is usefully interposed between the end face of the light conducting rod and the diode array.

This ensures that the light reaching the end face of the light conducting rod is made of sufficiently uniform distribution that the presence of varying light intensities at varying positions on the end face of the light conducting rod does not simulate error signals from the scanning beam. The light scattering element can usefully be a ground or opaline glass screen.

In order to loose as little light as possible the space between the light scattering element and the diode array is provided with an interior reflecting surface. A robust embodiment of especially advantageous construction is obtained by arranging the plate carrying the diode array and the light scattering element into a tube pushed on the end of the light conducting rod, if necessary the tube can also carry the interior reflecting surface.

The amplifier, which is connected directly to the diodes, and the current supply are also usefully incorporated into the tube.

In a further embodiment the diode array is arranged on the interior of a hollow sphere having a light scattering inner surface; the sphere being put on the end face of the light conducting rod and the diode array being in a region away from the region which directly receives light from the light conducting rod. The so called "Ulbricht's Sphere" is a suitable form of hollow sphere but must be modified to provide the aforementioned arrangement of diodes in its interior.

It is basically possible to connect all the diodes in parallel, by this means a high current sensitivity is achieved. The disadvantage of this arrangement is however that there is a very high self capacitance at the input to the processing circuit so that the limiting frequency of the circuit is relatively low. A series connection of the diodes is also basically possible which will produce a relatively high output potential. The disadvantage of this embodiment is however its very high internal resistance.

For these reasons the present invention preferably provides for the connection of fractions or subarrays of all the diodes in parallel to current voltage transformers whose outputs are passed to a summing amplifier. The current voltage transformers are usefully provided with positive feedback to neutralise the capacitive effects of the diodes. The maximum number of the parallel connected diodes depends on the highest cut of frequency which is to be transmitted. The summing of the signal from the individual current voltage transformers by a summing amplifier produces a considerable raising of the sensitivity without raising of the internal resistance as would result from direct series connection of the photo diodes.

An especial advantage of the construction in accordance with the invention is that in a further embodiment at least one diode can be used as a compensating diode for brightness compensation. To this end a time element is connected to the compensating diode by means of which the brightness compensation signal is formed.

The time element smooths the output signal and the time constant of the time element must be large in comparison with the duration of the received error measuring signal.

The output signal from the compensating diode or its associated current voltage transformer is usefully subtracted from the measuring signal in the summing amplifier. The individual signals are weighted so that when no measuring signal is present at the summing amplifier a null output signal exists. It is however also possible to sum the measurement signals from the current voltage transformers and then to process this signal in a difference amplifier with a corresponding weighting against the compensating signal.

In order that the low frequencies or the intermediate values of the measurement signals are simultaneously taken into account without impairing the value of the limiting frequency a further embodiment is provided in which a first sub-array of the diodes is connected to the summing amplifier by a circuit which passes only high frequency components and a further sub-array is connected to the summing amplifier by circuits which pass only direct current and low frequency components.

In the voltage current transformer it is preferable to use FET transistors in order to achieve low noise.

The time constant of the current supply for the circuit is kept relatively low by using a low input impedance amplifier and on account of the low capacities of the diodes. The output resistance is however chosen to be as large as is possible.

Embodiments the invention will now be described by way of example only and with reference to the accompanying drawings in which.

Figure 1:
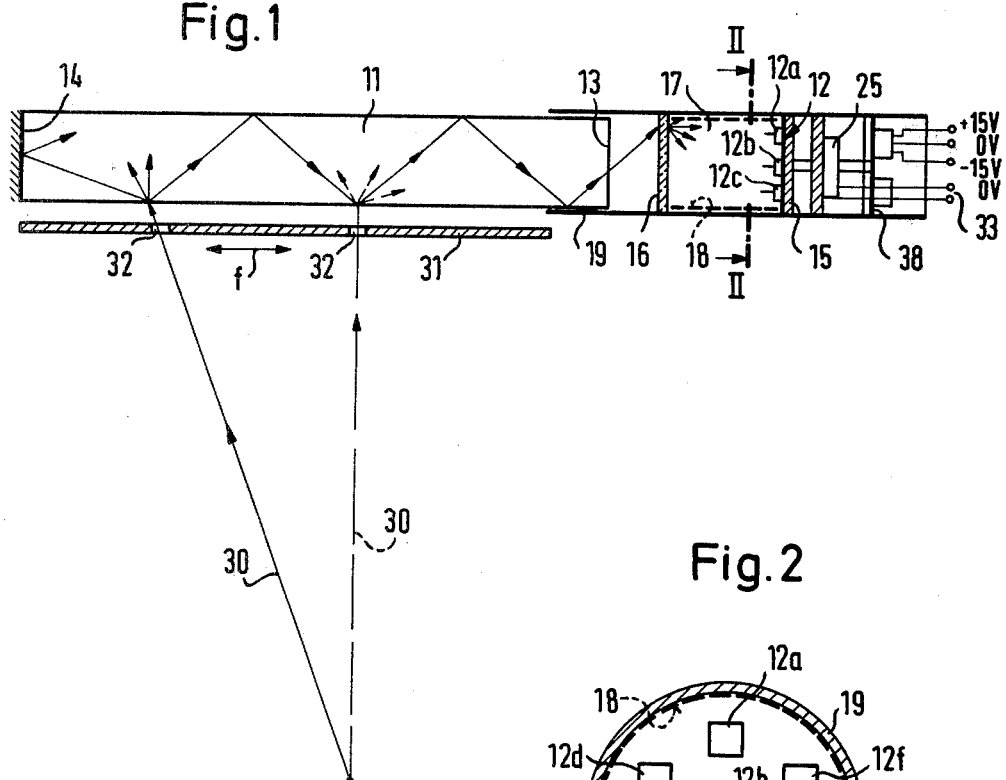
FIG. 1 shows a partly sectioned schematic side view of a photoelectric light detector.

In FIG. 1 there is shown in simplified form a band of material 31 which is capable of movement in a plane at right angles to the plane of the drawing. The band is scanned linewise in rapid succession in the direction of the double arrow F by a laser light beam.

Directly behind the band of material 31 is disposed, parallel to the scanning direction and to the material band 31, a light conducting rod 11 so that, for example, faults appearing as apertures 32 in the band allow light to fall at various positions on the surface of the light conducting rod 11. This light is passed by refraction and scattering to the inside of the light conducting rod and as is schematically indicated by arrows is totally reflected to the end faces 13, 14 of the light conducting rod. The end face 14 is provided with a reflecting surface so that light arriving there is reflected and finally after many internal reflections arrives in due course at the end face 13.

Figure 2:
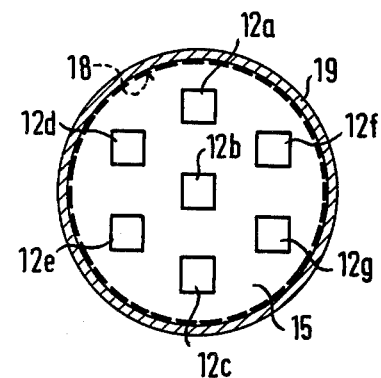
FIG. 2 is a section on the line II—II of FIG. 1.

In the vicinity of the end face 13 a tube 19 is pushed onto the light conducting rod and contains a ground glass screen 16 in the region of the end face 13. Spaced further away from the end face 13 is an array of photo diodes 12 arranged on a plate 15, the individual diodes of the array are shown in FIGS. 1 and 2 with the references 12a through to 12g. The diodes are regularly distributed over the face of the plate 15 and are packed as closely together as possible.

In the region of the space 17 between the ground glass screen 16 and the diode array the tube 19 has an interior reflecting surface 18 which is illustrated in broken lines.

Because of this construction the continually changing pattern of light on the end face 13 during the scanning process is so fogged and blurred that no error or measuring signal is produced in response to the different paths of the individual light rays in the light conducting rod.

Whilst the clearance between the ground glass screen 16 and the end face 13 should be small and preferably zero there must be provided a clearance between the ground glass screen 16 and the diode array 12. This clearance is preferably 3 to 5 times the diameter of the tube 19.

The internal reflecting surface 18 ensures that as little light as possible is lost.

Figure 3:
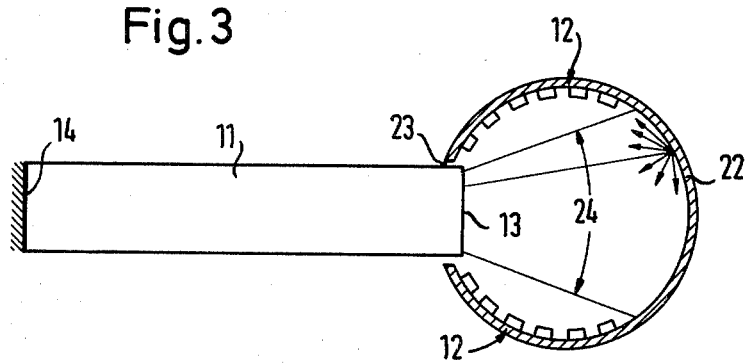
FIG. 3 is a view of a further embodiment shown similarly to FIG. 1.

Referring to FIG. 3 there can be seen an "Ulbricht hollow sphere" placed on the end of the light conducting rod 11 in the region of the end face 13. The correspondingly dimensioned opening 23 of the hollow sphere 22 surrounds the end face of the light conducting rod 11.

The solid angle through which light rays can leave the light conducting rod is determined by the angles of total reflection within the light conducting rod and is indicated by the reference numeral 24.

The photo diode array is, as shown, connected to the inner surface of the hollow sphere outside of the region directly receiving light from within the solid angle 24, this region is furthermore lined with a light scattering material.

Also by this means the irregularities of the light pattern on the end face 13 of the light conducting rod are removed.

Figure 4:
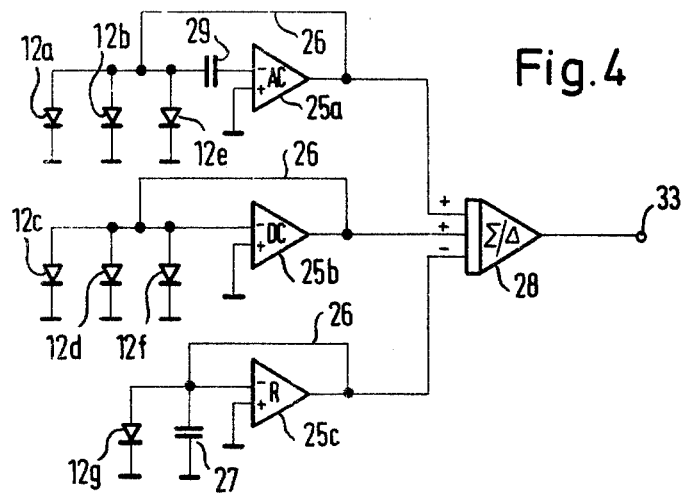
FIG. 4 is a simplified block circuit diagram of a electronic processing circuit for the photoelectric light detector.

In the arrangement of FIG. 4 several diodes are shown connected together in parallel, further diodes are optionally added to the array and from 8 to 32 are useful and 16 is especially preferred.

The diodes 12a, 12b and 12e are connected together by a high frequency coupling capacitor 29 to a current voltage transformer 25a whose output is connected to one input of a summing amplifier 28.

The further parallel connected diodes 12c, 12d and 12f are connected via a direct current voltage transformer 25b to a further input of the summing amplifier 28. Finally a compensating diode 12g which, by means of a parallel connected capacitor 27, is given a larger time constant is connected through a further current voltage transformer 25c to a subtracting input of a summing amplifier.

A positive feedback indicated at 26 results in an effective neutralising of the capacitive effects of the diodes.

The current voltage transformers 25 give preferably an amplification of 1 although the size of the amplification of the signals from the parallel connected diodes can be set to other values if desired.

Dependent on the size of the light conducting rod and the desired sensitivity further light transforming units similar to those formed by circuit elements 12a, 12b, 12e and 25a; 12c, 12d, 12f, 25b or 12g, 25c are provided and likewise connected to the summing amplifier 28.

The summed signals are so weighted that by subtraction of the compensating signal from the compensating diode 12g a null signal is achieved at the output 33 when no measurement signal is present. This means the prevailing background illumination is subtracted to leave only the measuring signal.

The high frequency stage with the current voltage transformer 25a has a high band width and is accordingly relatively insensitive. The direct current step with the current voltage transformer 25b has a smaller band width and is however intrinsically more sensitive.

Finally, the compensating diode with the transformer 25c has an intermediate band width and an intermediate sensitivity.

As can be seen from FIG. 2 the compensation diode is located in the midst of the measuring diodes.

Figure 5:
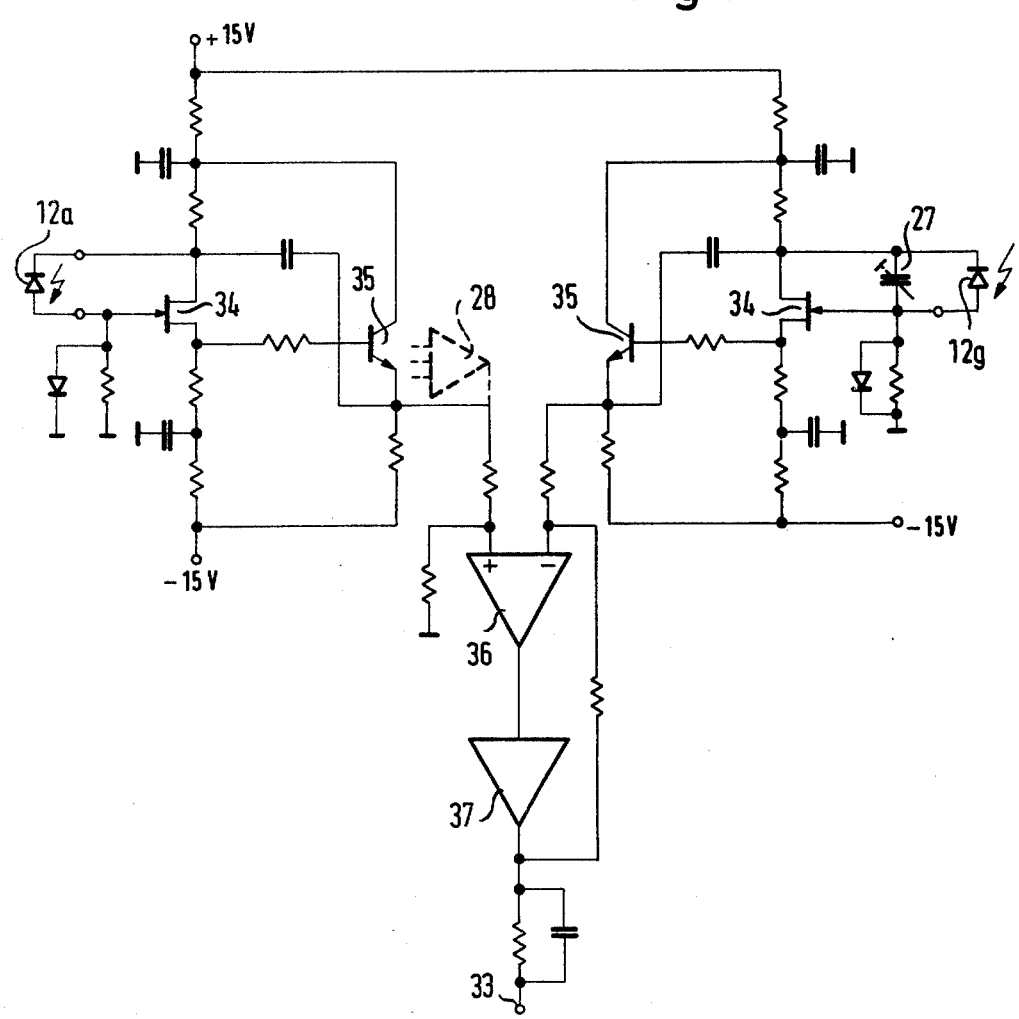
FIG. 5 is a detailed circuit diagram of an electronic processing circuit which for simplicity's sake reproduces only the circuit elements of a single measuring diode and the compensating diode.

FIG. 5 shows in detail the circuit of the current voltage transformer 25 for the examples of the photo diodes 12a and 12g.

The photo diodes 12a,g are respectively connected across transistors 34 which are direct current coupled to amplifying transistors 35. The outputs of the amplifier stages incorporating the transistors 35 are connected to the two inputs of a difference amplifier 36 in which a measurement signal is formed which is free from the influence of background illumination, and which is led via further amplifier 37 to the output 33.

From this point a measurement signal can be taken which relates only to faults in the band of material.

In parallel with the compensating diode 12g is connected a variable capacitor 27 by means of which the compensating diode circuit is given an adjustable and much larger time constant than the measuring diodes 12a,b etc. Thus an essentially constant signal is present at the compensating input to the difference amplifier 36.

Special attention is also drawn to the face that by the arrangement of one or more compensating diodes the effects of other long time influences such as the changing of the brightness of the lamp can be excluded. Also the unwelcome thermal drifts of such circuits can be removed by this means. Of especial advantage is the thermal coupling of the amplifying transistors 35. This can usefully be achieved by arranging all the circuits within the tube 19 of FIG. 1.

The current supply 38 for the individual circuit parts is also usefully arranged within the tube 19.

The box labelled 28 and shown in broken lines in FIG. 5 represents the summing amplifier 28. With the provision of further diodes the correspondingly weighted output from the summing amplifier 28 is connected to the plus input of the difference amplifier 36. It should also be mentioned that in FIG. 5 only one of the parallel connected diodes 12a, 12b or 12c is shown.

Of especial advantage for use with the present invention is the optical apparatus described and claimed in the simultaneously filed application with the title "Improvements in Optical Apparatus". The content of this simultaneously filed application will also be understood to form a part of the disclosure of the present application.

Further modifications to the embodiments will be readily appreciated by those skilled in the art for example the tube 19 may be used to screen the electrical components from electromagnetic radiation in particular it may be made from Mu-metal and the ground glass or opaline glass screen interposed between the end face of the light conducting rod and the photodiode array may be replaced with a screen comprising an array of individual lenses.

I claim:

1. A photoelectric light detection device suitable for being disposed at one end face of a light conducting rod and comprising an array of photodiodes, the array of photodiodes being subdivided into at least first and second sub-arrays of photodiodes and the photodiodes of each sub-array being connected together in parallel to a respective current voltage transformer and the outputs of the current voltage transformers being passed to a summing amplifier, there being provided a positive feedback from the output of each current voltage transformer to the photodiodes of the associated sub-array whereby the capacitive effect of each photodiode sub-array is at least partially compensated.

2. A photoelectric light detection device suitable for being disposed at one end face of a light conducting rod and comprising an array of photodiodes, the array of photodiodes being subdivided into at least first and second sub-arrays of photodiodes and the photodiodes of each sub-array being connected together in parallel to a respective current voltage transformer and the outputs of the current voltage transformers being passed to a summing amplifier, at least one of the photodiodes of said array being adapted to compensate for background illumination incident on the device.

3. A photoelectric light detection device suitable for being disposed at one end face of a light conducting rod and comprising an array of photodiodes including at least one compensation diode, electrical circuit means interconnecting said diodes to produce an electrical output signal representative of light received from said light conducting rod, said electrical circuit means including sub-circuit means for deriving a signal from said at least one compensation diode and representative of background light incident thereon and for subtracting this signal from the signals derived from the other said diodes whereby to compensate the photoelectric light detection device for the effects of background light.

4. A photoelectric light detection device according to claim 3 and in which, in addition to said compensation diode said array of photodiodes comprises at least first and second sub-arrays of photodiodes, the photodiodes of each sub-array being connected in parallel to a respective current voltage transformer, and wherein the outputs of the current voltage transformers are connected to a summing amplifier.

5. A photoelectric light detection device according to claim 3 and including further means for increasing the time constant of the sub-circuit means associated with said compensation diode for producing an improved compensation for background light.

6. A photoelectric light detection device according to claim 4 in which said sub-circuit means comprises means for passing the output of said at least one compensating photodiode to a respective current voltage transformer and for subsequently subtracting the output of this current voltage transformer from the signals from the other said current voltage transformers.

7. A photoelectric light detection device according to claim 4 and in which the first one of said sub-array of photodiodes is arranged in a circuit to allow the passage only of high frequency signals received from an associated light conducting rod, and the second said sub-array allows the passage only of direct current and low frequency signals received from the associated light conducting rod.

8. A photoelectric light detection device according to claim 4 and in which each said current voltage transformer includes a respective FET transistor.

9. A photoelectric light detection device according to claim 3 including means for spacing the photodiode array from an end face of an associated light conducting rod.

10. A photoelectric light detection device according to claim 9 and in which said spacing means includes a light scattering element.

11. A photoelectric light detection device according to claim 10 and in which the light scattering element comprises a ground glass screen.

12. A photoelectric light detection device according to claim 10 and in which the light scattering element comprises a screen of opaline glass.

13. A photoelectric light detection device according to claim 9 in which said light scattering element and the photodiode array are disposed within a tube, the end of said tube being adapted to fit the end of an associated light conducting rod.

14. A photoelectric light detection device according to claim 13 and in which said tube is arranged to screen the device from electro-magnetic radiation.

15. A photoelectric light detection device according to claim 14 and in which said tube comprises a metallic tube.

16. A photoelectric light detection device according to claim 3 and in which said photodiode array is arranged on a plate, said plate being disposed to face an end face of an associated light conducting rod.

17. A photoelectric light detection device according to claim 16 in which the size and shape of said plate is similar to the size and shape of the cross-section of an associated light conducting rod.

18. A photoelectric light detection device according to claim 10 in which there is provided structure having an internally reflecting surface between said light scattering element and said photodiode array.

19. A photoelectric light detection device according to claim 10 and in which said photodiode array and said light scattering element are spaced apart by a distance in the range three to five times the diameter of an associated light conducting rod.

20. A photoelectric light detection device according to claim 10 and in which said light scattering element is disposed so as to be spaced away from the end face of an associated light conducting rod by a distance which is small relative to the diameter of the light conducting rod.

21. A photoelectric light detection device according to claim 10 and in which said light scattering element contacts the end face of the light conducting rod.

22. A photoelectric light detection device according to claim 13 and in which the interior of said tube is provided with a reflecting interior surface.

23. A photoelectric light detection device according to claim 13 and further comprising an amplifier for the signal of the photodiode array, and a current supply for said amplifier, both said amplifier and said current supply being located within said tube.

24. A photoelectric light detection device according to claim 3 and further comprising a hollow sphere having an opening for receiving a light conducting rod, the interior surface of said sphere being reflecting, and said photodiode array being disposed on the inside surface of the sphere outside of the region capable of receiving light directly from the light conducting rod.

25. A photoelectric light detection device according to claim 4 and in which each of said sub-arrays contains a number of photodiodes in the range 8 to 32.

26. A photoelectric light detection device according to claim 25 and in which each said sub-array contains 16 photodiodes.

27. A photoelectric light detection device according to claim 2 in which a means are provided for increasing the time constant of a sub circuit including said compensating photodiode for producing an improved compensation for the background illumination.

28. A photoelectric light detection device according to claim 2 in which the output from said compensating photodiode is passed to a respective current voltage transformer and the output from said current voltage transformer is subsequently subtracted at the summing amplifier from the signals from the other said current voltage transformers.

* * * * *